United States Patent [19]

Holderbaum et al.

[11] Patent Number: 5,610,210
[45] Date of Patent: Mar. 11, 1997

[54] AMINOVINYLPHOSPHONIC ESTER STABILIZERS FOR ORGANIC MATERIAL

[75] Inventors: Martin Holderbaum, Ludwigshafen; Alexander Aumueller, Neustadt; Hubert Trauth, Dudenhofen, all of Germany

[73] Assignee: BASF Aktiengesellschaft, Ludwigshafen, Germany

[21] Appl. No.: 495,581

[22] PCT Filed: Jan. 29, 1994

[86] PCT No.: PCT/EP94/00254

§ 371 Date: Aug. 9, 1995

§ 102(e) Date: Aug. 9, 1995

[87] PCT Pub. No.: WO94/18210

PCT Pub. Date: Aug. 18, 1994

[30] Foreign Application Priority Data

Feb. 9, 1993 [DE] Germany .......................... 43 03 648.1

[51] Int. Cl.[6] ...................... C08K 5/5373; C08K 5/5333; C07F 9/06; C07C 229/00
[52] U.S. Cl. ..................... 524/99; 524/102; 524/131; 524/132; 546/22; 546/24; 558/167; 558/168; 558/169
[58] Field of Search .................. 558/167, 168, 558/169; 546/22, 24; 524/99, 131, 132, 102

[56] References Cited

U.S. PATENT DOCUMENTS

| 3,079,366 | 2/1963 | Boyle et al. | |
| 3,462,439 | 8/1969 | Popoff et al. | 546/22 |
| 3,885,912 | 5/1975 | Golborn et al. | |
| 4,388,252 | 6/1983 | Duersch et al. | |
| 5,260,286 | 11/1993 | Lawson et al. | 546/22 |

FOREIGN PATENT DOCUMENTS

| 1911768 | 10/1969 | Germany . |
| 45-14284 | 5/1970 | Germany . |
| 1253611 | 11/1971 | United Kingdom . |

OTHER PUBLICATIONS

*Phosphorus and Sulfur*, 1987, vol. 31, pp. 231–243.

*Primary Examiner*—Veronica P. Hoke
*Attorney, Agent, or Firm*—Oblon, Spivak, McClelland, Maier & Neustadt, P.C.

[57] ABSTRACT

Aminovinylphosphonic esters I

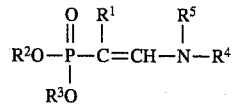

where
$R^1$ is cyano, a radical of the formula —CO—OR[6] or a group of the formula

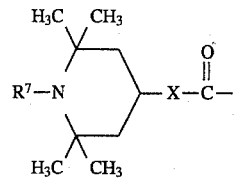

$R^2$, $R^3$ and $R^6$ are $C_1$–$C_{20}$-alkyl, $C_5$–$C_8$-cycloalkyl, $C_7$–$C_{18}$-aralkyl, phenyl or tolyl, $R^4$ is an unsubstituted or substituted phenyl or heterocyclic group defined below $R^5$ is hydrogen or $C_1$–$C_{12}$-alkyl, $R^7$ is hydrogen, $C_1$–$C_6$-alkyl, formyl, $C_2$–$C_6$-alkanoyl, $C_1$–$C_{12}$-alkoxy, $C_5$- or $C_6$-cycloalkoxy, cyanomethyl, 2-hydroxyethyl, benzyl or a radical of the formula —CR[8]=CH—CO—OR[6], $R^8$ is hydrogen, $C_1$–$C_6$-alkyl or a radical of the formula —CO—OR[6], and X is oxygen or NH, are used as light, oxygen and heat stabilizers for organic material.

9 Claims, No Drawings

AMINOVINYLPHOSPHONIC ESTER STABILIZERS FOR ORGANIC MATERIAL

The present invention relates to the use of aminovinylphosphonic esters of the general formula I

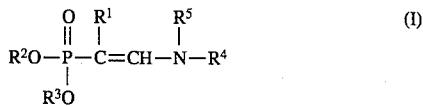

where
$R^1$ is cyano, a radical of the formula —CO—$OR^6$ or a group of the formula

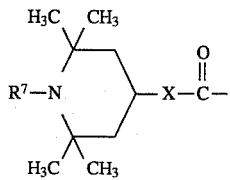

$R^2$, $R^3$ and $R^6$ are $C_1$–$C_{20}$-alkyl, $C_5$–$C_8$-cycloalkyl, $C_7$–$C_{18}$-aralkyl, phenyl or tolyl, $R^4$ is phenyl which may be substituted by one to three $C_1$–$C_{12}$-alkyl groups, $C_1$–$C_{12}$-alkoxy groups, halogen atoms, cyano groups, hydroxyl groups, phenyl groups or groups of the formula —CO—$OR^6$, —CO—$R^6$, —CO—$NHR^6$, —O—CO—$R^6$ or —NH—CO—$R^6$, or is a five-membered or six-membered unsaturated or saturated heterocyclic ring having up to three heteroatoms selected from the group consisting of nitrogen, oxygen and sulfur, which may additionally be benzofused and may be substituted by one to three $C_1$–$C_{12}$-alkyl groups, $C_1$–$C_{12}$-alkoxy groups, halogen atoms, cyano groups, hydroxyl groups, phenyl groups, phenoxy groups or $C_1$–$C_{12}$-alkoxycarbonyl groups, or is a group of the formula

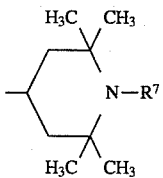

$R^5$ is hydrogen or $C_1$–$C_{12}$-alkyl,
$R^7$ is hydrogen, $C_1$–$C_6$-alkyl, formyl, $C_2$–$C_6$-alkanoyl, $C_1$–$C_{12}$-alkoxy, $C_5$- or $C_6$-cycloalkoxy, cyanomethyl, 2-hydroxyethyl, benzyl or a radical of the formula —$CR^8$=CH—CO—$OR^6$,
$R^8$ is hydrogen, $C_1$–$C_6$-alkyl or a radical of the formula —CO—$OR^6$, and
X is oxygen or NH,
as light stabilizers and stabilizers for organic material.

Since some of the compounds I are novel substances, the present invention also relates to these novel substances.

The present invention furthermore relates to organic material stabilized to the action of light, oxygen and heat by means of the compounds I, in particular stabilized plastics and coatings.

It is known that organic material, in particular plastics and coatings, is very rapidly destroyed, particularly by the action of light. This destruction usually manifests itself in yellowing, discoloration, cracking or embrittlement of the material. The intention is therefore to use light stabilizers and stabilizers to achieve satisfactory protection from the destruction of organic material by light, oxygen and heat.

Thus, U.S. Pat. No. 3,079,366 (1) describes, inter alia, alkyl 3-(arylamino)-2-cyanoacrylates and alkyl 3-(arylamino)-2-(alkoxycarbonyl)acrylates as light stabilizers for plastics.

Some of the compounds I are known from the literature. Thus, German Laid-Open Application DOS 1,911,768 (2) relates to, inter alia, phosphonic esters having α-(alkoxycarbonyl)-β-($C_6$- or $C_7$-arylamino)vinyl groups; these compounds are recommended as reagents for aldehyde synthesis, in particular for formyl olefination. Phosphorus and Sulfur, 31 (1987), 231–243 (3), discloses the compound diethyl α-cyano-β-(phenylamino)vinylphosphonate. However, neither (2) nor (3) refers to the use as a light stabilizer or stabilizer.

The excessively low compatibility of the plastics, the excessively short duration of the protective effect, the natural color of the substances, the tendency to volatility and thermal decomposition of the stabilizers during incorporation at elevated temperatures are frequently unsatisfactory in the case of the stated prior art compounds.

It is an object of the present invention to provide light stabilizers or stabilizers which more effectively protect organic material.

We have found that this object is achieved by the aminovinylphosphonic esters I defined at the outset.

Examples of suitable straight-chain or branched alkyl radicals for $R^2$, $R^3$ and $R^5$ to $R^8$ and as substituents on the phenyl nucleus and on heterocyclic rings and as the alcohol radical in alkoxycarbonyl groups, which are referred to as $C_1$–$C_6$-alkyl, $C_1$–$C_{12}$-alkyl and $C_1$–$C_{20}$-alkyl radicals, are methyl, ethyl, n-propyl, isopropyl, n-butyl, isobutyl, sec-butyl, tert-butyl, n-amyl, isoamyl, sec-amyl, tert-amyl, neopentyl, n-hexyl, n-heptyl, n-octyl, 2-ethylhexyl, n-nonyl, isononyl, n-decyl, n-undecyl, n-dodecyl, n-tridecyl, isotridecyl, n-tetradecyl, n-pentadecyl, n-hexadecyl, n-heptadecyl, n-octadecyl and n-eicosyl. In general lower alkyl, especially $C_1$–$C_4$-alkyl, in particular methyl and ethyl, are preferred.

Particularly suitable straight-chain or branched $C_2$–$C_6$-alkanoyl radicals $R^7$ are acetyl, as well as propionyl, butyryl, isobutyryl, pentanoyl and hexanoyl.

Particularly suitable straight-chain or branched $C_1$–$C_{12}$-alkoxy groups for $R^7$ and as substituents on phenyl nucleus and on heterocyclic rings are $C_1$–$C_4$-alkoxy, such as methoxy, ethoxy, n-propoxy, isopropoxy, n-butoxy, isobutoxy, sec-butoxy and tert-butoxy, as well as n-pentyloxy, n-hexyloxy, isohexyloxy, n-heptyloxy, isoheptyloxy, n-octyloxy, 2-ethylhexyloxy, isooctyloxy, n-nonyloxy, n-decyloxy, n-undecyloxy and n-dodecyloxy.

$C_5$- or $C_6$-Cycloalkoxy $R^7$ is in particular cyclopentyloxy or cyclohexyloxy.

Where $R^7$ is a radical of the formula —$CR^8$=CH—CO—$OR^6$, $R^8$ is preferably $C_1$–$C_4$-alkoxycarbonyl, especially methoxycarbonyl or ethoxycarbonyl, or in particular hydrogen.

Particularly suitable $C_5$–$C_8$-cycloalkyl radicals $R^2$, $R^3$ and $R^6$ are $C_5$- or $C_6$-cycloalkyl, such as cyclopentyl or cyclohexyl, as well as cycloheptyl, cyclooctyl, methylcyclopentyl, dimethylcyclopentyl, methylcyclohexyl, ethylcyclohexyl or dimethylcyclohexyl.

Examples of suitable $C_7$–$C_{18}$-aralkyl-radicals $R^2$, $R^3$ and $R^6$ are naphthylmethyl, diphenylmethyl and methylbenzyl, in particular $C_7$–$C_{18}$-phenylalkyl, such as 1-phenylethyl, 2-phenylethyl, 1-phenylpropyl, 2-phenylpropyl, 3-phenylpropyl, 2-phenyl-prop-2-yl, 4-phenylbutyl, 2,2-dimethyl-2-phenylethyl, 5-phenylamyl, 10-phenyldecyl, 12-phenyldodecyl or in particular benzyl.

Suitable tolyl radicals are ortho-, meta- and especially paratolyl.

Halogen atoms are to be understood as meaning fluorine and iodine, but especially bromine and in particular chlorine.

Suitable five-membered or six-membered unsaturated or saturated heterocyclic rings having up to three heteroatoms selected from the group consisting of nitrogen, oxygen and sulfur, which may additionally be benzofused and substituted by the radicals defined are:

tetrahydrofuran, furan, tetrahydrothiophene, thiophene, pyrrolidin, pyrroline, pyrrole, isoxazole, oxazole, thiazole, pyrazole, imidazoline, imidazole, 1,2,3-triazolidine, 1,2,3- and 1,2,4-triazole, 1,2,3-, 1,2,4- and 1,2,5-oxadiazole, tetrahydropyran, dihydropyran, 2H- and 4H-pyran, piperidine, 1,3- and 1,4-dioxane, morpholine, pyrazan, pyridine, pyrimidine, pyridazine, pyrazine, 1,2,5-oxathiazine, 1,3,5-, 1,2,3- and 1,2,4-triazine, benzofuran, thionaphthene, indoline, indole, isoindoline, benzoxazole, indazole, benzimidazole, chromane, isochromane, 2H- and 4H-chromene, quinoline, isoquinoline, 1,2,3,4-tetrahydroisoquinoline, cinnoline, quinazoline, quinoxaline, phthalazine and benzo-1,2,3-triazine.

Where substituted phenyl radicals occur as radicals $R^4$, the preferred degree of substitution is 2 or, in particular, 1. Monosubstituted phenyl radicals are ortho-, meta- or, preferably, parasubstituted, disubstituted phenyl radicals often have a 2,4 substitution pattern and trisubstituted phenyl radicals often have a 2,4,6 substitution pattern. Where two or three substituents occur, they may be identical or different.

With regard to the three-dimensional position of the substituents at the C—C double bond in the compounds I, the structure I comprises both the relevant E isomers and the Z isomers. Mixtures of the two isomers can of course also occur.

A preferred embodiment involves the use of aminovinylphosphonic esters I in which $R^1$ is cyano or $C_1$–$C_{12}$-alkoxycarbonyl.

Another preferred embodiment involves the use of aminovinylphosphonic esters I in which $R^2$ and $R^3$ are each $C_1$–$C_6$-alkyl.

A further preferred embodiment involves the use of aminovinylphosphonic esters I in which $R^4$ is phenyl which may be substituted by one or two $C_1$–$C_4$-alkyl groups, $C_1$–$C_4$-alkoxy groups, chlorine atoms, cyano groups, hydroxyl groups or $C_1$–$C_4$-alkoxycarbonyl groups, or is a six-membered unsaturated or saturated heterocyclic ring which has up to three nitrogen atoms and may additionally be benzofused and substituted by one or two $C_1$–$C_4$-alkyl groups, $C_1$–$C_4$-alkoxy groups, chlorine atoms, cyano groups, hydroxyl groups or $C_1$–$C_4$-alkoxycarbonyl groups, or is a group of the formula

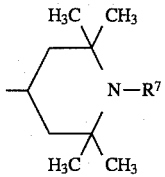

and $R^5$ is hydrogen.

Particularly suitable heterocyclic rings $R^4$ are pyridine, 2-, 3- and 4-methylpyridine, pyrimidine, pyridazine, pyrazine and 1,3,5-triazine.

The aminovinylphosphonic esters I used according to the invention can be prepared by methods known per se. The preparation can be carried out, for example, by reacting a cyanomethanephosphonic ester or phosphonoacetic ester with a trialkyl orthoformate, in particular triethyl orthoformate or trimethyl orthoformate, and an aromatic or heterocyclic amine.

The compounds I can furthermore be prepared by reacting a dimethylaminomethylenecyanomethanephosphonic ester or dimethylaminomethylenephosphonoacetic ester with an aliphatic amine, eg. triacetonediamine.

The reaction is advantageously carried out in a suitable polar organic solvent, such as an alcohol, eg. n-propanol, n-butanol, ethylene glycol, diethylene glycol, ethylene glycol monomethyl ether, cyclohexanol or a similar compound. Other suitable solvents are carboxamides, such as N,N-dimethylformamide, or excess trialkyl orthoformate. If the starting compounds used form a liquid mixture, an additional solvent can be dispensed with.

In the case of very long reaction times, if desired additional Lewis acids, such as boric acid, $AlCl_3$, $ZrCl_4$, $TiCl_4$ or especially $ZnCl_2$, may be used as catalysts for the reaction, in the amounts required for this purpose.

If, in the compounds I, $R^7$ is an acrylic ester group of the formula —$CR^8$=CH—CO—$OR^6$, compounds I in which $R^7$ is hydrogen are advantageously reacted with acetylenecarboxylic acid derivatives, such as propiolic esters or acetylenedicarboxylic esters, for the preparation of such compounds.

The compounds I used according to the invention are very useful for stabilizing organic material to the action of light, oxygen and heat. They are also effective as metal deactivators. They are added to the organic material to be stabilized in a concentration of from 0.01 to 5, preferably from 0.02 to 2%, by weight, based on the organic material, before, during or after its preparation.

Organic material is to be understood as meaning, for example, cosmetic preparations, such as ointments and lotions, drug formulations, such as pills and suppositories, photographic recording materials, in particular photographic emulsions, or intermediates for plastics and coatings, in particular plastics and coatings themselves.

The present invention furthermore relates to organic materials stabilized to the action of light, oxygen and heat, in particular plastics and coatings which contain the compounds I in the above-mentioned concentrations.

All known apparatuses and methods for mixing stabilizers or other additives into polymers may be used for mixing the compounds I used according to the invention, especially with plastics.

The organic materials stabilized by the compounds I used according to the invention may, if required, contain further additives, for example antioxidants, light stabilizers, metal deactivators, antistatic agents, flame retardants, pigments and fillers.

Antioxidants and light stabilizers which may be added in addition to the compounds I used according to the invention are, for example, compounds based on sterically hindered phenols or sulfur- or phosphorus-containing costabilizers.

Examples of such phenolic antioxidants are 2,6-di-tert-butyl-4-methylphenol, n-octadecyl β-(3,5-di-tert-butyl-4-hydroxyphenyl)propionate, 1,1,3-tris(2-methyl-4-hydroxy-5-tert-butylphenyl)butane, 1,3,5-trimethyl-2,4,6-tris(3,5-di-tert-butyl-4-hydroxybenzyl)benzene, 1,3,5-tris(3,5-di-tert-butyl-4-hydroxybenzyl) isocyanurate, 1,3,5-tris[β-(3,5-di-tert-butyl-4-hydroxybenzyl)propionylethyl] isocyanurate, 1,3,5-tris(2,6-dimethyl-3-hydroxy-4-tert-butylbenzyl) isocyanurate and pentaerythrityl tetrakis[β-3,5-di-tert-butyl-4-hydroxy-phenyl)propionate].

Examples of suitable phosphorus-containing antioxidants are tris(nonylphenyl) phosphite, distearyl pentaerythrityl diphosphite, tris(2,4-di-tert-butylphenyl) phosphite, tris(2-tert-butyl-4-methylphenyl)phosphite, bis(2,4-di-tert-butylphenyl) pentaerythrityl diphosphite and tetrakis(2,4-di-tert-butylphenyl) 4,4'-biphenylene diphosphite.

Examples of sulfur-containing antioxidants are dilauryl thiodipropionate, dimyristyl thiodipropionate, distearyl thiodipropionate, pentaerythrityl tetrakis(β-laurylthiopropionate) and pentaerythrityl tetrakis(β-hexylthiopropionate).

Further antioxidants and light stabilizers which may be used together with the compounds I are, for example, 2-(2'-hydroxyphenyl)benztriazoles, 2-hydroxybenzophenones, aryl esters of hydroxybenzoic acids, α-cyanocinnamic acid derivates, benzimidazolecarboxanilides, nickel compounds and oxalic acid dianilides.

Particularly good stabilization is achieved if at least one further light stabilizer from the class consisting of the sterically hindered amines is added in the usual concentration to the compounds I.

Examples of further sterically hindered amines which are suitable for this purpose are bis(2,2,6,6-tetramethylpiperidyl) sebacate, bis(1,2,2,6,6-pentamethylpiperidyl) sebacate, the condensate of 1-hydroxyethyl-2,2,6,6-tetramethyl-4-hydroxypiperidine with succinic acid, the condensate of N,N'-(2,2,6,6-tetramethylpiperidyl)hexamethylendiamine with 4-tert-octylamino-2,6-dichloro-1,3,5-triazine, tris(2,2,6,6-tetramethylpiperidyl) nitrilotriacetate, tetrakis(2,2,6,6-tetramethyl-4-piperidyl)-1,2,3,4-butanetetracarboxylic acid, 1,1'-(1,2-ethanediyl)-bis-3,3,5,5-tetramethylpiperazinone) and the condensates of 4-amino-2,2,6,6-tetramethylpiperidines with tetramethylolacetylenediureas.

Examples of plastics which may be stabilized by the compounds I used according to the invention are:

polymers of mono- and diolefins, such as low density and high density polyethylene, polypropylene, linear polybut-1-ene, polyisoprene, polybutadiene and copolymers of mono- or diolefins or blends of the stated polymers;

copolymers of mono- or diolefins with other vinylmonomers, such as ethylene/alkyl acrylate copolymers, ethylene/alkyl methacrylate copolymers, ethylene/vinyl acetate copolymers or ethylene/acrylic acid copolymers;

polystyrene and copolymers of styrene or α-methylstyrene with dienes and/or acryloyl derivates, such as styrene/butadiene, styrene/acrylnitrile (SAN), styrene/ethyl methacrylate, styrene/butadiene/ethyl acrylate, styrene/acrylonitrile/methacrylate, acrylonitril/butadiene/styrene (ABS) or methyl methacrylate/butadiene/styrene (MBS);

halogen-containing polymers, such as polyvinyl chloride, polyvinyl fluoride, polyvinylidene fluoride and copolymers thereof;

polymers which are derived from α,β-unsaturated acids and derivatives thereof, such as polyacrylates, polymethacrylates, polyacrylamides and polyacrylnitriles;

polymers which are derived from unsaturated alcohols and amines or from their acryloyl derivatives or acetals, for example polyvinyl alcohol and polyvinyl acetate;

polyurethanes, polyamides, polyureas, polyesters, polycarbonates, polysulfones, polyethersulfones and polyetherketones.

The compounds I used according to the invention may also be employed for stabilizing surface coatings, for example industrial coatings. Particularly noteworthy among these are baking finishes, and among these in turn automotive finishes, preferably two-coat finishes, are particularly noteworthy.

The compounds I used according to the invention may be added to the coating in solid or dissolved form. Their good solubility in coating systems is particularly advantageous.

The compounds I used according to the invention are preferably used for stabilizing polyurethanes, polyesters, polystyrene, polyolefins, such as ethylene polymers or propylene polymers, polyamides and ABS and SAN polymers, in particular for stabilizing molding materials obtained therefrom and for stabilizing surface coatings, in particular comprising acid-curable coatings.

A further preferred field of use is the stabilization of polypropylene and polyamide fibers.

The compounds I used according to the invention exhibit good compatibility with the conventional types of plastic and good solubility and excellent compatibility in conventional coating systems. They have as a rule no natural color or only a very slight natural color, are stable at the conventional temperatures for processing plastics and coatings, are nonvolatile and in particular provide long-term protection for the materials treated with them.

With the exception of the aminovinylphosphonic esters known from the publications (2) and (3), the compounds I are novel substances.

Accordingly, the present invention also relates to aminovinylphosphonic esters of the general formula II

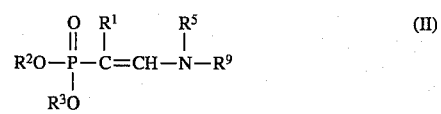

where $R^9$ is phenyl which is substituted by one to three $C_2$–$C_{12}$-alkyl groups, $C_1$–$C_{12}$-alkoxy groups, halogen atoms, cyano groups, hydroxyl groups, phenyl groups or groups of the formula —CO—OR$^6$, —CO—R$^6$, —CO—NHR$^6$, —O—CO—R$^6$ or —NH—CO—R$^6$, or $R^9$ is a five-membered or six-membered unsaturated or saturated heterocyclic ring which has up to three heteroatoms selected from the group consisting of nitrogen, oxygen and sulfur and may additionally be benzofused and substituted by one to three $C_1$–$C_{12}$-alkyl groups, $C_1$–$C_{12}$-alkoxy groups, halogen atoms, cyano groups, hydroxyl groups, phenyl groups, phenoxy groups or $C_1$–$C_{12}$-alkoxycarbonyl groups, or $R^9$ is a group of the formula

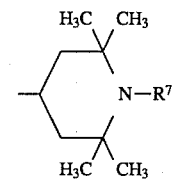

and the other variables have the abovementioned meanings.

The present invention furthermore relates to aminovinylphosphonic esters of the general formula III

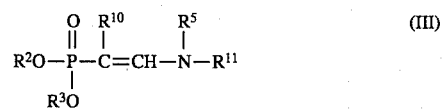

where $R^{10}$ is a radical of the formula —CO—OR$^6$ or a group of the formula

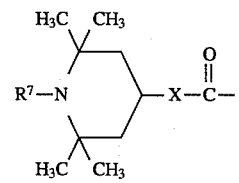

$R^{11}$ is phenyl or tolyl and the remaining variables have the abovementioned meanings.

The examples which follow illustrate the invention. The preparation conditions were not optimized.

PREPARATION EXAMPLES

EXAMPLE 1

35.4 g (0.2 mol) of diethylphosphonoacetonitrile, 33 ml (0.2 mol) of triethyl orthoformate and 21.4 g (0.2 mol) of 4-aminotoluene were slowly heated to 120° C. and stirred for 5 hours. The ethanol formed was distilled off. Thereafter, the mixture was cooled, suspended in ethanol and stirred for 1 hour at room temperature. The suspension was then filtered under suction and the residue was washed with ethanol. 20 g of diethyl α-cyano-β-(4-methylphenylamino)vinylphosphonate were obtained in the form of colorless crystals of melting point 116° C.

The spectroscopic data is shown in Table 1.

EXAMPLES 2 TO 8

The products shown in Table 1 were prepared from diethylphosphonoacetonitrile similarly to Example 1, using the corresponding aromatic or heterocyclic amines. The melting points and the spectroscopic data of the products are also shown in Table 1.

EXAMPLE 10

The compound of the following formula was obtained from triacetonediamine and triethyl dimethylaminomethylenephosphonoacetate similarly to Example 9, in form of colorless crystals of melting point 76° C.:

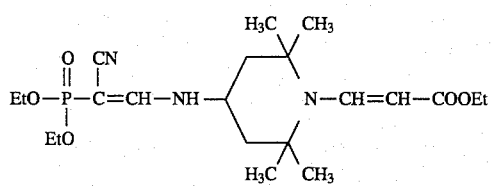

EXAMPLE 11

24 g (0.07 mol) of the compound from Example 9 were refluxed with 9.8 g (0.1 mol) of ethyl propiolate in 50 ml of ethanol for 3 hours. Thereafter, the mixture was cooled and the precipitate was filtered off with suction and washed with a little ethanol. 24.0 g of colorless crystals of melting point 245°–247° C. and of the formula

TABLE 1

Structure, melting point and spectroscopic data of the products of Examples 1 to 8 of the general formula

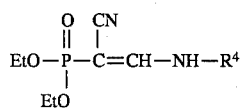

| Example No. | R⁴ | Melting point [°C.] | UV data (CH₃OH) $\lambda_{max}$ [nm] | $\epsilon$ |
|---|---|---|---|---|
| 1 | 4-Methylphenyl | 116 | 309 | 23700 |
| 2 | Phenyl | 116 | 304 | 25000 |
| 3 | 3,5-Dimethylphenyl | 125 | 307 | 23700 |
| 4 | 4-Ethoxycarbonylphenyl | 135–138 | 319 | 41600 |
| 5 | 4-Chlorophenyl | 130 | 309 | 23700 |
| 6 | 2-Pyridinyl | 121–123 | 269/313 | 15500/29100 |
| 7 | 6-Methyl-2-pyridinyl | 143 | 269/316 | 16000/30600 |
| 8 | 5-Methyl-2-pyridinyl | 138 | 275/318 | 18200/29100 |

EXAMPLE 9

18.7 g (0.12 mol) of triacetonediamine and 18.7 g (0.12 mol) of diethyl (N,N-dimethylaminomethylene)cyanomethanephosphonate (prepared from diethyl cyanomethanephosphonate and N,N-dimethylformamide acetal) in 50 ml of ethanol were refluxed for 6 hours with the addition of 4 drops of concentrated hydrochloric acid. Thereafter, the mixture was cooled, and the precipitate formed was filtered off with suction and washed with diethyl ether. 15.6 g of colorless crystals of melting point 255° C. (decomposition) and of the formula

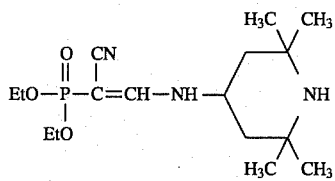

were obtained.

were obtained.

Spectroscopic data: $\lambda_{max}$ (CH₃OH)=281 nm, $\epsilon$=44800

EXAMPLE 12

The compound of the following formula was obtained from the compound from Example 10 and ethyl propiolate similarly to Example 11, in the form of colorless crystals of melting point 141° C.

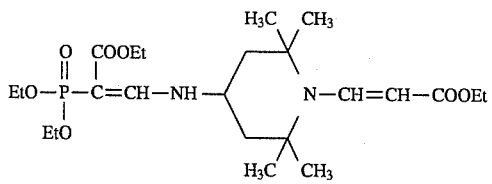

Spectroscopic data: $\lambda_{max}$ (CH$_3$OH)=283 nm, $\epsilon$=50200

USE EXAMPLES

For the preparation of ABS exposure samples, 0.5% by weight of the sterically hindered amine of the formula IV and 0.5% by weight of the aminovinylphosphonic ester shown in Table 2 were dissolved in ABS of the Terluran® 967 K type (unpigmented) by extruding once at a melt temperature of 250° C., and the resulting granules were injection molded at 260° C. to give 2 mmthick moldings.

The lightfastness and weatherfastness of the injection moldings were tested in an accelerated weathering apparatus of the Xenotest® 1200 type.

A measure of the yellowing and hence of the photooxidative degradation of the polymer, as a function of the weathering time, is the yellowness index (YI), according to Annual Book of ASTM Standards D 1925-70 (reapproved 1977), which increases with increasing yellowness.

The stabilizer mixtures used and the results of the exposure are listed in Table 2.

ABS injection moldings without a stabilizer and ABS injection moldings containing a mixture of the sterically hindered amine IV and the cyanoacrylic ester V known from (1) served for comparison.

TABLE 2

| YI values after accelerated weathering (Xenotest ® 1200) | | |
|---|---|---|
| Stabilizer mixture | 0 h | after 600 h |
| according to the invention | | |
| 0.5% by weight of IV + 0.5% by weight of Example 1 | 43 | 25 |
| 0.5% by weight of IV + 0.5% by weight of Example 2 | 42 | 28 |
| 0.5% by weight of IV + 0.5% by weight of Example 3 | 41 | 26 |
| for comparison: without stabilizer | 38 | 52 |
| for comparison: 0.5% by weight of IV + 0.5% by weight of V | 43 | 29 |

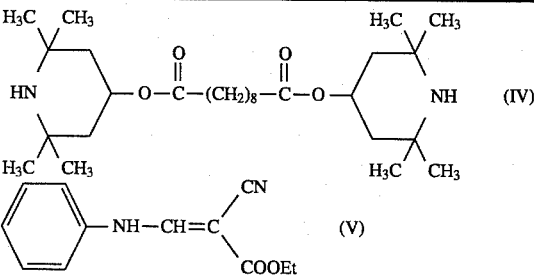

We claim:

1. A method for stabilizing an organic material to the action of light, oxygen and heat, comprising adding to said organic material an aminovinylphosphonic ester of the formula I

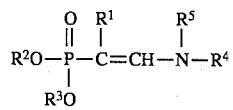

where $R^1$ is cyano, a radical of the formula —CO—OR$^6$ or a group of the formula

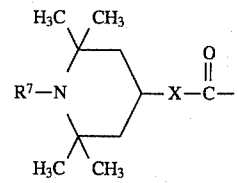

$R^2$, $R^3$ and $R^6$ are $C_1$–$C_{20}$-alkyl, $C_5$–$C_8$-cycloalkyl, $C_7$–$C_{18}$-aralkyl, phenyl or tolyl, $R^4$ is phenyl which may be substituted by one to three $C_1$–$C_{12}$-alkyl groups, $C_1$–$C_{12}$-alkoxy groups, halogen atoms, cyano groups, hydroxyl groups, phenyl groups or groups of the formula —CO—OR$^6$, —CO—R$^6$, —CO—NHR$^6$, —O—CO—R$^6$ or —NH—CO—R$^6$, or is a five-membered or six-membered unsaturated or saturated heterocyclic ring having up to three hetero atoms selected from the group consisting of nitrogen, oxygen and sulfur, which may additionally be benzofused and may be substituted by one to three $C_1$–$C_{12}$-alkyl groups, hydroxyl groups, phenyl groups, phenoxy groups or $C_1$–$C_{12}$-alkoxycarbonyl groups, wherein said heterocyclic ring is attached to the nitrogen of formula I through a carbon atom on said ring, or is a group of the formula

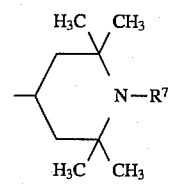

$R^5$ is hydrogen or $C_1$–$C_{12}$-alkyl, $R^7$ is hydrogen, $C_1$–$C_6$-alkyl, formyl, $C_2$–$C_6$-alkanoyl, $C_1$–$C_{12}$-alkoxy, $C_5$- or $C_6$-cycloalkoxy, cyanomethyl, 2-hydroxyethyl, benzyl or a radical of the formula —CR$^8$=CH—CO—OR$^6$, $R^8$ is a hydrogen, $C_1$–$C_6$-alkyl or a radical of the formula —CO—OR$^6$, and X is oxygen or NH.

2. The method as claimed in claim 1, wherein $R^1$ is cyano or $C_1$–$C_{12}$-alkoxycarbonyl.

3. The method as claimed in claim 1, wherein $R^2$ and $R^3$ are each $C_1$–$C_6$-alkyl.

4. The method as claimed in claim 1, wherein $R^4$ is phenyl which may be substituted by one or two $C_1$–$C_4$-alkyl groups, $C_1$–$C_4$-alkoxy groups, chlorine atoms, cyano groups, hydroxyl groups or $C_1$–$C_4$-alkoxycarbonyl groups, or is a six-membered unsaturated or saturated heterocyclic ring which has up to three nitrogen atoms and may additionally be benzofused and substituted by one or two $C_1$–$C_4$-alkyl groups, $C_1$–$C_4$-alkoxy groups, chlorine atoms, cyano groups, hydroxyl groups or $C_1$–$C_4$-alkoxycarbonyl groups, or is a group of the formula

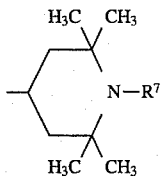

and $R^5$ is hydrogen.

5. The method of claim 1, wherein said organic material is a plastic or coating.

6. An organic material stabilized to the action of light, oxygen and heat and containing from 0.01 to 5% by weight, based on the amount of the organic material, of one or more aminovinylphosphonic esters I as claimed in claim 1.

7. A plastic or coating stabilized to the action of light, oxygen and heat and containing from 0.01 to 5% by weight, based on the amount of the plastic or coating, of one or more aminovinylphosphonic esters I as claimed in claim 1.

8. An aminovinylphosphonic ester of the formula II

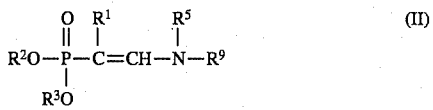

where $R^9$ is phenyl which is substituted by one to three $C_2$–$C_{12}$-alkyl groups, $C_1$–$C_{12}$-alkoxy groups, halogen atoms, cyano groups, hydroxyl groups, phenyl groups or groups of the formula —CO—OR$^6$, —CO—R$^6$, —CO—NHR$^6$, —O—CO—R$^6$ or —NH—CO—R$^6$, or $R^9$ is a five-membered or six-membered unsaturated or saturated heterocyclic ring having up to three hetero atoms selected from the group consisting of nitrogen, oxygen and sulfur and may additionally be benzofused and substituted by one to three $C_1$–$C_{12}$-alkyl groups, $C_1$–$C_{12}$-alkoxy groups, halogen atoms, cyano groups, hydroxyl groups, phenyl groups, phenoxy groups or $C_1$–$C_{12}$-alkoxycarbonyl groups, wherein said heterocyclic ring is attached to the nitrogen of formula II through a carbon atom on said ring, or $R^9$ is a group of the formula

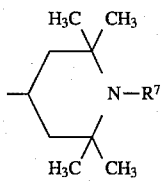

$R^1$ is cyano, a radical of the formula —CO—OR$^6$ or a group of the formula

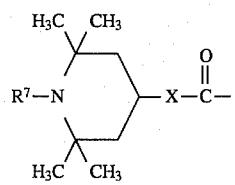

$R^2$, $R^3$ and $R^6$ are $C_1$–$C_{20}$-alkyl, $C_5$–$C_8$-cycloalkyl, $C_7$–$C_{18}$-aralkyl, phenyl or tolyl, $R^5$ is hydrogen or $C_1$–$C_{12}$-alkyl, $R^7$ is hydrogen, $C_1$–$C_6$-alkyl, formyl, $C_2$–$C_6$-alkanoyl, $C_1$–$C_{12}$-alkoxy, $C_5$- or $C_6$-cycloalkoxy, cyanomethyl, 2-hydroxyethyl, benzyl or a radical of the formula —CR$^8$=CH—CO—OR$^6$, $R^8$ is hydrogen, $C_1$–$C_6$-alkyl or a radical of the formula —CO—OR$^6$, and X is oxygen or NH.

9. An aminovinylphosphonic ester of the formula III

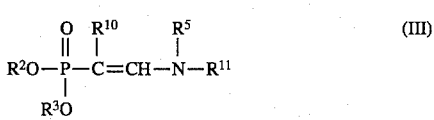

where $R^{10}$ is a radical of the formula —CO—OR$^{12}$ or a group of the formula

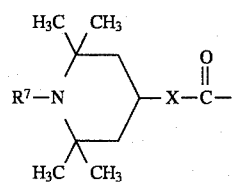

$R^{11}$ is phenyl or tolyl $R^2$, $R^3$ and $R^6$ are $C_1$–$C_{20}$-alkyl, $C_5$–$C_8$-cycloalkyl, $C_7$–$C_{18}$-aralkyl, phenyl or tolyl, $R^{12}$ is $C_5$–$C_8$-cycloalkyl, $C_7$–$C_{18}$-aralkyl, phenyl or tolyl, $R^5$ is hydrogen or $C_1$–$C_{12}$-alkyl, $R^7$ is hydrogen, $C_1$–$C_6$-alkyl, formyl, $C_2$–$C_6$-alkanoyl, $C_1$–$C_{12}$-alkoxy, $C_5$- or $C_6$-cycloalkoxy, cyanomethyl, 2-hydroxyethyl, benzyl or a radical of the formula —CR$^8$=CH—CO—OR$^6$, $R^8$ is hydrogen, $C_1$–$C_6$-alkyl or a radical of the formula —CO—OR$^6$, and X is oxygen or NH.

* * * * *